United States Patent [19]

Schlutz

[11] 4,091,989

[45] May 30, 1978

[54] CONTINUOUS FLOW FRACTIONATION AND SEPARATION DEVICE AND METHOD

[76] Inventor: Charles A. Schlutz, 7081 NW. 10th Pl., Plantation, Fla. 33313

[21] Appl. No.: 756,724

[22] Filed: Jan. 4, 1977

[51] Int. Cl.² .......................... B04B 5/04; B04B 15/12
[52] U.S. Cl. ................................ 233/14 R; 233/19 R; 233/27
[58] Field of Search ................ 233/1 D, 14 R, 16, 17, 233/26, 27, 28, 32, 34, 38, 40, 46, 15, 1 R, 1 A

[56] References Cited

U.S. PATENT DOCUMENTS

| 717,385 | 12/1902 | Gathmann | 233/17 |
|---|---|---|---|
| 1,429,320 | 9/1922 | Bouillon | 233/14 R |
| 1,644,492 | 10/1927 | Rawolle | 233/14 R |
| 3,347,454 | 10/1967 | Bellamy et al. | 233/14 R |
| 3,561,672 | 2/1971 | Schlutz et al. | 233/17 |
| 3,655,123 | 4/1972 | Judson et al. | 233/28 X |
| 3,982,691 | 9/1976 | Schlutz | 233/15 X |

*Primary Examiner*—George H. Krizmanich
*Attorney, Agent, or Firm*—Murray & Whisenhunt

[57] ABSTRACT

A centrifuge apparatus is provided for separating red blood cells and other dense solids from a suspending liquid. An enclosure means encloses liquid suspended red blood cells and is rotatable about its axis. An injector means moves the liquid suspended blood cells into and the separated blood cells out of the enclosure means and a seal means seals the injector means to the enclosure means in a liquid-tight relationship. A plurality of red blood cells receiving means are spaced about the periphery of the enclosure means and are serially connected by ducts. Suspending liquid, passing from receiving means to receiving means, will be at least partially depleted of red blood cells after passing through each receiving means. An intake passage moves liquid suspended red blood cells from the injector means into the first red blood cell receiving means and a discharge passage passes essentially blood cell-free suspending liquid from the last blood cell receiving means to the injector means and into an external receptacle.

76 Claims, 5 Drawing Figures

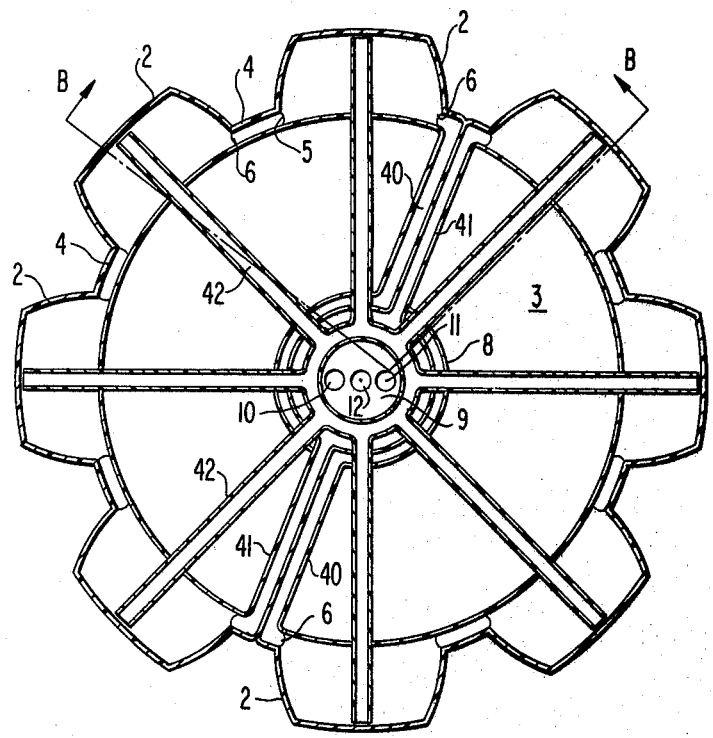
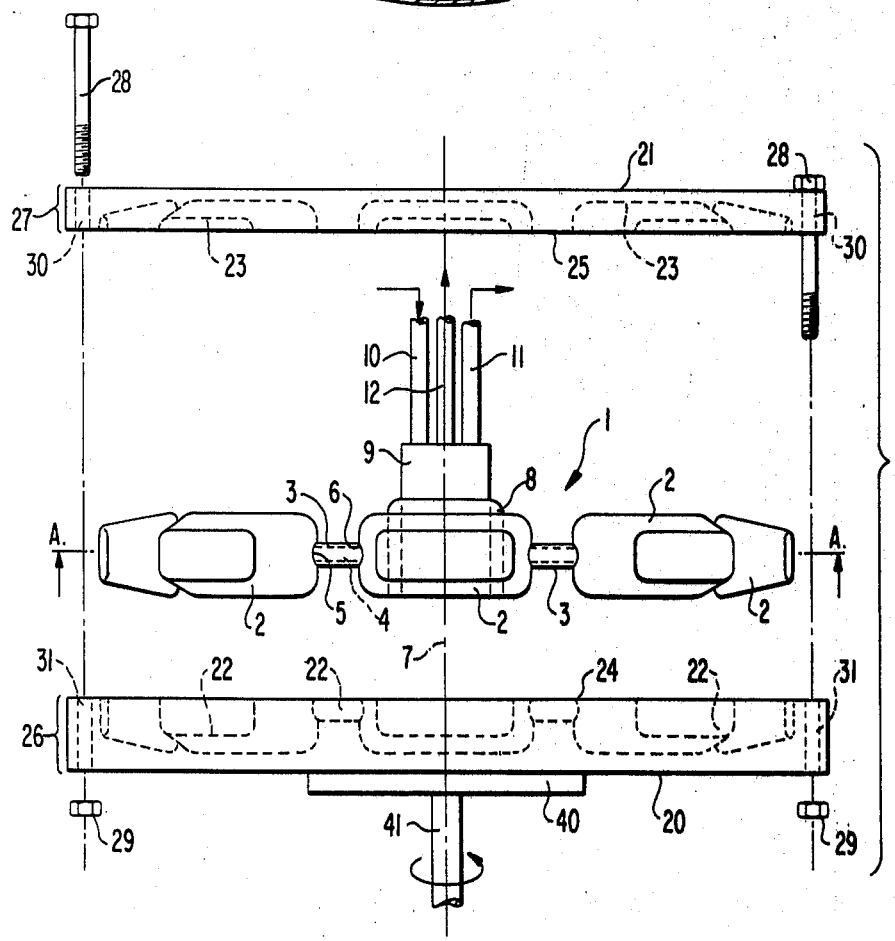
FIG 2
FIG 1

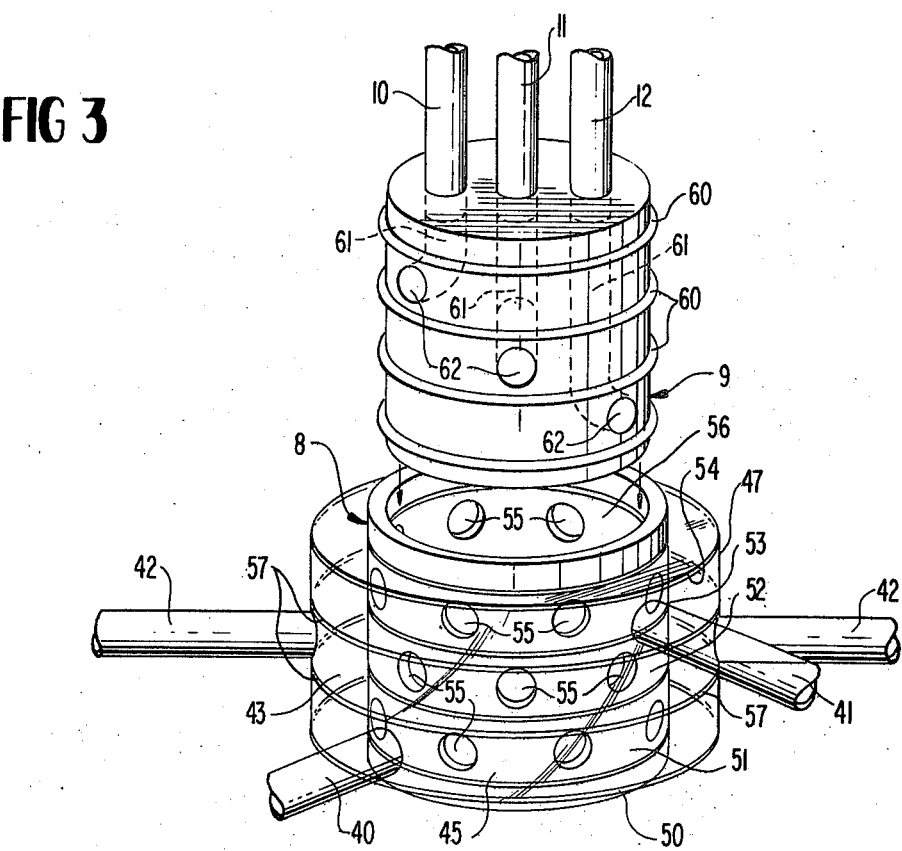

CONTINUOUS FLOW FRACTIONATION AND SEPARATION DEVICE AND METHOD

The present invention relates to a centrifuge device and method for fractionation and separation of a finely-divided solid particulate material suspended in a liquid. The device and method have special applicability where the separated solid particulate material must be substantially recovered from the suspending liquid, and particularly where the separation of the particulate material must be accomplished in an isolated environment, for example in a pre-sterilized environment. Thus, the invention has a special utility for fractionating and separating biological particulate material from a suspending liquid, and especially the fractionation and separation of solid blood components from a suspending liquid, e.g., plasma, salinic solutions and the like, or whole blood. An important embodiment is the fractionation, separation and recovery of red blood cells from whole blood.

BACKGROUND OF THE INVENTION

Centrifuge devices and methods of the present general nature are known to the art. These devices and methods are characterized by their ability to separate finely-divided particulate material from a suspending liquid, where the particulate material is to be substantially recovered and/or where the particulate material must be separated or washed or the like in an isolated environment. Thus, devices and methods of this nature have their greatest utility in connection with the separation and/or washing of solid blood components from whole blood or from a liquid blood fraction. The present invention is likewise applicable to such devices and methods, and thus, while the present invention has broader utility than the separation of blood components and extends to the breadth indicated above, the invention will be principally hereinafter described in terms of the embodiment of separation of solid blood components, for the sake of conciseness.

In prior co-pending application Ser. No. 714,651, which is a divisional application of Ser. No. 513,509, now U.S. Pat. No. 3,982,261, it is noted that human blood obtained from donors often contains unwanted contaminants such as toxins, viruses, medicants, bacteria and glycerine. These contaminants render that blood unsuitable for direct transfusion. The art has proposed various devices and methods for separating and washing the blood to remove those unwanted contaminants. The more accepted devices and methods to accomplish the foregoing are based upon centrifugal separation of the red blood cells from the blood fluids with a subsequent counter-flow washing of the blood cells to remove the contaminants. For purposes of the present specification and claims, the term "blood cells" is defined to mean all solid blood components, including red blood cells, leukocytes and platelets ("buffy coat"). After the blood cells have been adequately washed, they are removed from the devices, often by re-suspending in a suitable liquid, such as a sterile salinic solution, Locke-Ringer solution or human serum albumin. The cells are aseptically transferred from the devices into a sterile package. U.S. Pat. No. 3,347,454, issued to the present applicant is representative of this art. An improvement in this art is also provided by U.S. Pat. No. 3,561,672, issued to the present applicant, wherein disposable receptacles are provided which can receive a plurality of units of blood for washing in a single centrifuge operation. These disposable receptacles avoid the necessity of a thorough cleaning of the centrifuge after processing each donor's unit of blood. The operation of this device is described in some detail in Schlutz and Bellamy, *Continuous Flow Cell Washing System*, TRANSFUSION, Vol. 8, No. 5, Sept. Oct. 1968, and a pre-packaged combination of two receptacles, associated seal devices and conduits is described in detail by Schlutz and Bellamy in *A Disposable Counterflow System for Washing Erythrocytes in a Centrifugal Field*, Proc. 12th Congr., Int. Soc. Blood Transf., Moscow 1969 Bibl. Haemat, No. 38, Part II, pp. 350-358 (Karger, Basel, 1971). Thus, the art has available considerable details regarding the operation and mechanical construction of centrifuges of the present nature as well as associated equipment for such centrifuges and those details will not be repeated herein. The entire disclosures of the above noted patents and publications are incorporated herein by reference and relied upon for the aforementioned details.

In application Ser. No. 714,651, a device and method are described where the efficiency of washing of blood cells is substantially increased in a centrifugal operation. That device includes an enclosure for enclosing liquid suspended blood cells wherein a plurality of angularly shaped blood cell receiving means are evenly spaced about the periphery of the enclosure. Each blood cell receiving means has at least one pair of opposite wall portions which converge toward the longitudinal periphery of the enclosure and form a locus of maximum centrifugal force in the rotating enclosure at the apex formed by the juncture of the converging wall portions. A conduit is disposed in the angularly shaped receiving means and terminates at or near the locus of maximum centrifugal force. An injector moves suspended blood cells into the enclosure and removes separated and washed cells from the conduit. Appropriate seal means provide for the enclosure means to be rotated about its vertical axis while maintaining a liquid-tight seal. The liquid suspended blood cells flow through the injector and into the enclosure and distribution of the suspended blood cells about the enclosure is accomplished by rotation of the enclosure. With further rotation the blood cells are separated and compacted in the angularly shaped receiving means. A wash liquid is then flowed through the conduits and the wash liquid therefore enters each receiving means at the furthest peripheral point and passes back through the compacted blood cells, thus, insuring complete washing of the blood cells. After the washing is completed, the blood cells may or may not be suspended in a suitable fluid, e.g. a salinic solution, and flowed out of the apparatus via the conduits.

As can be appreciated from the foregoing, the primary function performed by these prior devices is the separating of all of the blood cells from the suspending liquid, washing all of the blood cells, and then removing all of the blood cells from the devices. Thus, these devices do not function to effect any separation of the various blood cells, e.g. red blood cells from formed elements (platelets, etc.) and leukocytes or to recover so separated red blood cells.

However, in certain circumstances it would be a decided advantage in the art to separate red blood cells from other cells, i.e. the other formed elements, and provide such separated red cells substantially free of the other formed solid blood elements, e.g. the leukocytes and platelets, and, further, recover such red blood cells in a non-suspended form. Such recovered red blood cells are of considerable value in correcting the anemia of patients who are candidates for tissue transplants or for patients who require continued replenishment of red cells. For example, if whole blood is given to replenish the depleted supply of red blood cells, often the required volume of whole blood during a period of time exceeds the total liquid volume which can be contained in the body circulatory system without the risk of causing congestion in the kidney, heart and lung (hypervolemia). Additionally, when whole blood is given only for the purpose of replenishing red blood cells, the unnecessary additional leukocytes and platelets which the patient receives can produce severe, perhaps, fatal reactions. For example, in transplant patients, the transfusion of leukocytes may initate transplant rejections. When blood cells are separated and/or washed according to the prior methods an inconsequential portion of the leukocytes and platelets are removed and the risks of severe reactions or transplant rejections remain.

As can be appreciated, therefore, the prior devices and methods are not satisfactory for use in treating diseases and conditions which primarily affect the red blood cell population. It would be, however, of decided advantage in the art to provide devices and methods for separating red blood cells and providing such cells which are substantially free from leukocytes and platelets and which cells can be recovered in a substantially non-suspended form. Such methods and devices, of course, must be capable of functioning in a practical manner to recover practical amounts of red blood cells. Additionally, such devices and methods must be capable of recovering those red blood cells in such a manner as to not introduce foreign contaminants such as airborne bacteria, solid particulate matter and the like. Of even further advantage would be the ability of such devices and methods to recover the red blood cells in a device which is pre-sterilized.

OBJECTS OF THE INVENTION

Therefore, in view of the above, it is an object of the invention to provide methods and devices wherein centrifugal separation of liquid suspended red blood cells can be performed in such a manner that the red blood cells are substantially leukocyte and platelet free. It is a further object of the invention to provide such separation in a manner that the red blood cells may be recovered in a substantially non-suspended form, e.g. as packed red blood cells. It is a further object of the invention to provide such recovered red blood cells which are essentially leukocyte and platelet-free and, conversely, to provide leukocytes and platelets which are red blood cell-free. It is yet a further object of the invention to provide devices and methods whereby the separation and recovery of the red blood cells can be performed in an apparatus which may be pre-sterilized. It is yet a further object of the invention to provide such devices and methods which can recover red blood cells in a practical manner and in practical quantity so that the devices and methods may be conveniently used by technologists in local hospitals and like institutions for recovery of red cells. It is still a further object of the invention to provide such devices and methods wherein the separation and recovery of the red blood cells may be accomplished in a disposable structure of a design and configuration which can be relatively cheaply manufactured and conveniently used, so that the risk of contamination of a succeeding processed unit of blood by unwanted contaminants in a preceeding unit of blood is eliminated. Other objects will be apparent from the following disclosure and claims.

BRIEF DESCRIPTION OF THE INVENTION

Briefly stated, the present invention provides a centrifugal apparatus for separating red blood cells from their suspending liquid. The apparatus comprises an enclosure means for enclosing liquid suspended red blood cells. The enclosure means is preferably disposable and also collapsible. Rotation means rotate the enclosure about the vertical axis thereof. Injector means move liquid suspended red blood cells into and the separated red blood cells out of the enclosure means. Associated with the injector means is a seal means for sealing the injector means to the enclosure means in a liquid-tight relationship, which also insures that the device and method may be operating in a sterile condition. A plurality of red blood cell receiving means, in fluid communication with each other, are spaced about the longitudinal periphery of the enclosure means and form part of the enclosure means. Each of the red blood cell receiving means has an entry duct means for passing the liquid suspended red blood cells into the receiving means and an exit duct means for passing from the receiving means the partially red blood cell depleted suspending liquid. A part of the red blood cells will remain in the receiving means, hence, partially depleting the red blood cells from the suspending liquid. The exit duct means of each red blood cell receiving means is in fluid communication with the entry duct means of the next succeeding red blood cell receiving means, thus, forming a passageway between succeeding red blood cell receiving means. The entry and exit duct means are of a vertical cross-sectional area which is small compared with the vertical cross-sectional area of the receiving means, i.e., a cross-section ratio of at least 1:2, respectively, and more preferably at least 1:3 or 1:6, e.g., at least 1:10. The peripheral extremity of the receiving means lies on a peripherial diameter of the enclosure means which is larger than the peripheral diameters of the enclosure means on which the entry and exit duct means lie, i.e., at least 5% larger, e.g., at least 7% or 10% larger. As can be appreciated, therefore, the duct means are substantially inwardly toward the axis of rotation as compared with the more distal position of the red blood cell receiving means. Further, the volume of each receiving means will be large compared with the volume of the entry and exit duct means, i.e., at least twice as large, e.g., at least four or eight times as large.

An intake passage means is in fluid communication with the injector means for passing liquid suspended red blood cells from the injector means into the entry duct means of the first blood cell receiving means or directly into the first blood cell receiving means. Similarly, a discharge passage means is in fluid communication with the injector means for passing the essentially red blood cell-free suspending liquid from the exit duct means of the last red blood cell receiving means to the injector means (including communication through one or more receiving means without an independent duct means, as explained hereinafter). It can be appreciated that this provides a continuous path for entry of the liquid suspended red blood cells, separation and compaction of the red blood cells and passing of the suspending liquid which has been separated from the red blood cells out of the device. It will also be appreciated that since the volumetric capacity of the red blood cell receiving means will be large in comparison with the volumetric capacity of the duct means that during operation of the device suspending liquid will be removed therefrom. For example, when whole blood is involved, the volume of the red blood cells will be from about 38 to 52% of the total blood volume. This volume will correspond to the volume of the total red blood cell receiving means. This will require that the liquid portion of the blood (also containing the leukocytes and platelets) will be totally expelled from the device during operation thereof, with the exception of that minimal volume which remains in the ducts.

The separated red blood cells may be unloaded simply by pumping the cells back through the intake passageway or on through the discharge passageway. In this method a bleed of sterile air into the enclosure means via the opposite passageway, i.e., the discharge passageway and intake passageway respectively, will facilitate the red blood cell removal. Also, if the enclosure means or at least the red blood cell receiving means are constructed of a collapsible or semi-rigid material and a differential pressure is exerted thereacross to cause collapsing thereof, the red blood cell removal will be further facilitated. However, a preferred embodiment is that of providing a plurality of independent conduit means, each with one end thereof in fluid communication with the injector means and the other end thereof disposed in the blood cell receiving means and preferably near the peripheral extremity of the blood cell receiving means. By applying a differential pressure across the collapsible enclosure, or at least red blood cell receiving means, the separated and compacted red blood cell will be forced out of the blood cell receiving means and through the independent conduit to the injector and out of the apparatus. These methods allow recovery of the red blood cells without the necessity of re-suspending those red blood cells in any liquid, other than the liquid remaining with the red blood cells during the separation process. It has been unexpectedly and surprisingly found that this liquid does not contain significant detectable leukocytes or platelets and it is not necessary to wash the separated and conpacted red blood cells to remove leukocytes or platelets therefrom. Generally speaking, the amount of this liquid associated with the separated red blood cells will be in the order of 10% by volume or less.

Power means are provided for rotating the rotating means and enclosure means to a speed of angular rotation sufficient to separate the red blood cells from the suspending liquid and other formed elements and compact the red blood cells in the red blood cell receiving means.

Control means are provided for controlling the flow of liquid suspended red blood cells through the injector means, intake passage means, entry duct means of the first red blood cell receiving means, and for controlling the flow of suspending liquid from the exit duct means of the last red blood cell receiving means through the discharge passageway and out through the injector. Also, while not necessary, but in the preferred embodiment, the control means controls the flow of separated red blood cells from the red blood cell receiving means through the independent conduit means and through the injector.

Thus, as can be appreciated, the function of the apparatus is that the liquid suspended red blood cells move from the injector means to the first red blood receiving means and by centrifugal force the more dense red blood cells separate from the less dense suspending liquid and other formed elements and compact at the peripheral extremity of the red blood cell receiving means and the suspending liquid is trans-elutriated (as explained more fully hereinafter) via the exit duct means of the first red blood cell receiving means and the entry duct means of the next succeeding red blood cell receiving means to the next succeeding red blood cell receiving means. This function is repeated with each succeeding red blood cell receiving means and essentially total separation of the red blood cells from the other formed elements and the suspending liquid is, thus, accomplished. The product recovered from the device is, therefore, essentially leukocyte and platelet-free red blood cells.

After completion of the centrifuge operation, the duct means and the innermost extremities of the red blood cell receiving means will contain suspending liquid and in unloading the device some of that suspending liquid will be removed with the separated red blood cells. If it is desired to eliminate that suspending liquid, a wash liquid is used to flush away the suspending liquid. In this embodiment, the control means includes a wash means for washing the unbound interface of the separated red blood cells by passing a washing fluid through the apparatus in the same path as the path of the suspended red blood cells. Since the receiving means are already full of the compacted red blood cells, except at the innermost extremities thereof, the wash fluid will sweep the inner extremities of the red blood cell receiving means and the ducts and replace the suspending liquid with the wash fluid. Alternatively, the wash fluid may enter the enclosure means via the independent conduit means and be removed from the enclosure means via the intake or discharge passageway. The wash fluid is suitably a salinic solution or pre-treated and cleansed autologus plasma, or the like.

It can therefore be seen that the device and method of the present invention accomplished the objects described above.

BRIEF DESCRIPTION OF THE DRAWINGS

FIG. 1 is an exploded elevation view of the major components of a representative embodiment of the centrifuge apparatus and the enclosure means.

FIG. 2 is a cross-sectional view of the enclosure means of FIG. 1 taken along the line A—A.

FIG. 3 is a schematic perspective view of a representative embodiment of an injector means and associated seal means suitable for use with the present invention.

FIG. 5 is a partial enlargement of FIG. 2 along the line B—B.

DETAILED DESCRIPTION OF THE INVENTION

Figure 4:
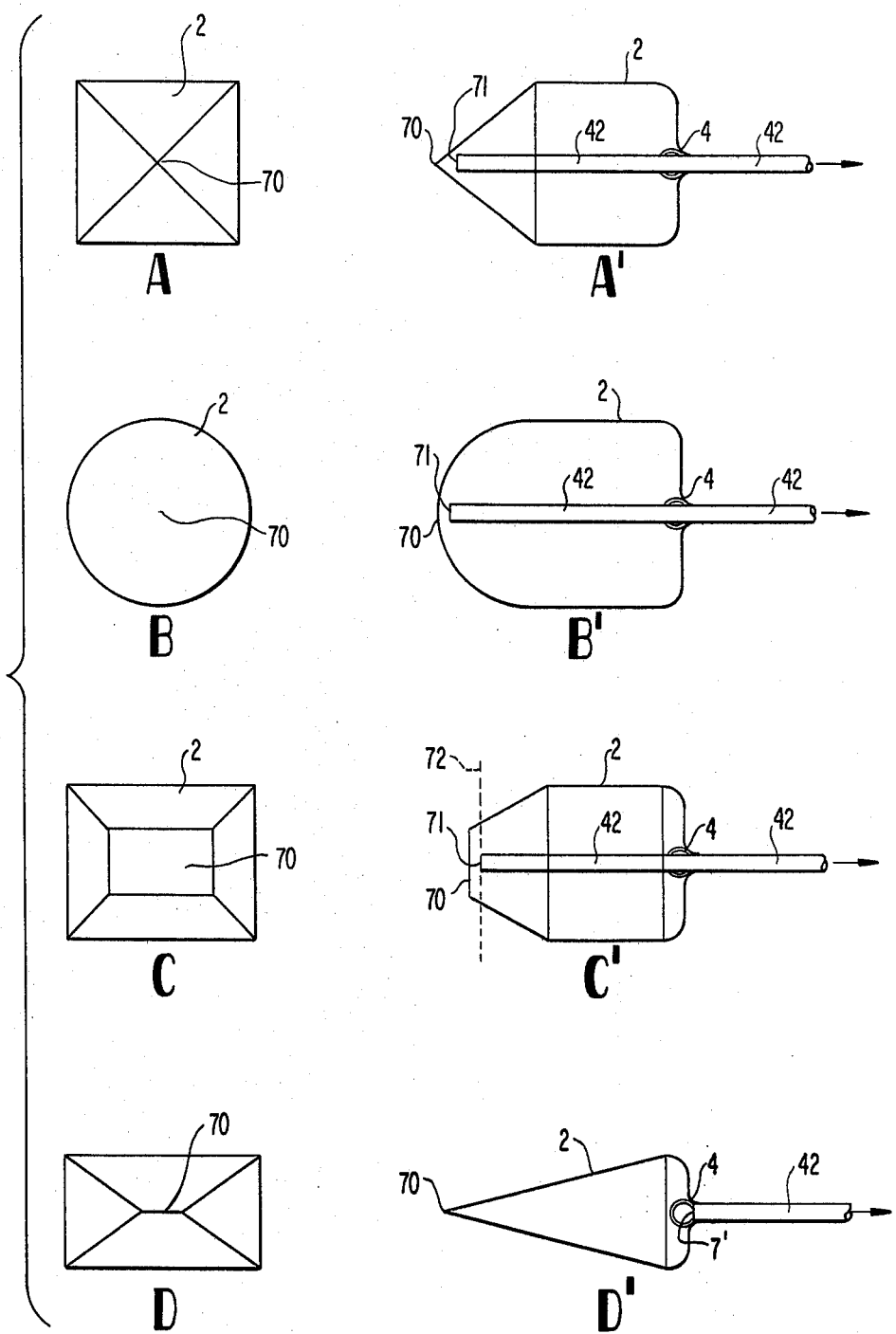
FIG. 4 is a schematic illustration of representative shapes of the red blood cell receiving means which are suitable for use with the present invention.

The major components of the present device are best understood from FIG. 1. The enclosure means, generally 1, consists of a plurality of red blood receiving means 2 which are connected by a land 3 which has disposed therein duct 4 which is for definitional purposes identified as exit duct 5 of one red blood cell receiving means and entry duct 6 of the next red blood cell receiving means.

At the vertical axis 7 of the enclosure, is disposed a seal means 8, and disposed therein is an injector means 9. The injector means has associated therewith a loading passageway 10 for introducing suspended red blood cells into the device and a discharge duct means 11 for removing suspending liquid and other formed elements. Separated red blood cells may be removed from the apparatus via unloading passageway 12, although other arrangements may be used as more fully explained hereinafter.

For medical purposes the enclosure means is preferably, although not necessarily, constructed of a collapsible material, such as a semi-rigid inert plastic. The plastic should be capable of resisting sterilization conditions without significant deterioration and of medically acceptable grade. This provides a relatively inexpensive and disposable enclosure means, which is, of course, necessary for practical medical application.

In view of this nature of the materials used for constructing the enclosure means for medical purposes, it is necessary that the enclosure means be contained within a supporting structure for rotation during the centrifuging operation. Thus, there is provided a supporting structure consisting of a lower table 20 and an upper table 21. The tables are suitably made of steel or other rigid material capable of withstanding the centrifugal forces generated during operation of the centrifuge. Lower Table 20 may have an internal configuration 22 which essentially duplicates the outside configuration of the lower portion of enclosure 1. Similarly, upper Table 21 has an interior configuration 23 which essentially duplicates the upper configuration of an enclosure 1. As will be explained hereinafter, the enclosure may be conveniently manufactured by heat sealing together an upper and lower portion thereof. If the heat seal, for example, is formed along the horizontal centerline of the enclosure (along A—A of FIG. 1) then it is preferred that the mating surfaces 24 and 25 of support Tables 20 and 21, respectively, do not follow that same centerline, since as will be appreciated, a solid, rather than the abutting mated surface will provide a stronger support. Thus, as shown in FIG. 1, conveniently, lower support Table 20 may have a depth 26 which is greater than depth 27 of upper support Table 21. Of course, the vice versa could be used.

The enclosure means is held in support Tables 20 and 21 by any convenient mechanical means and FIG. 1 illustrates a combination of bolts 28 and nuts 29 through corresponding bolt holes 30 and 31.

The assembled centrifuge is rotated by way of rotation support Table 40 and rotation shaft 41 which is conveniently coupled to a power source (not shown) by any convenient mechanical drive means (not shown).

FIG. 2 is a cross-section along lines A—A of FIG. 1. The red blood cell receiving means 2 are inter-connected by exit ducts 5 and entry ducts 6 which form, in combination, the continuous inter-connecting duct 4. Duct 4 is shown for illustration purposes, and as a preferred embodiment of the invention, but the specification and claims are to be understood to include the embodiment where exit duct 5 and entry duct 6 (forming duct 4) are a single opening with no length of duct or no substantially length of duct between adjoining receiving means. The intake passageway 40, as shown in FIG. 2, is split so as to provide balance for the enclosure means during loading thereof while rotating. Thus, each half of the illustration of FIG. 2 will operate in the same manner as the other half. For purposes of conciseness of discussion, therefore, the operation will be disclosed in connection with only one half of the enclosure means.

Intake passageway 40 is in fluid communication with seal means 8, which seal means is in turn in fluid communication with injector 9. Injector 9 has loading passageway 10 for moving suspended red cells and suspending liquid or wash liquid from the injection means, discharge duct means 11 for discharging suspending liquid and other formed elements and unloading passage 12 for removing separated red blood cells from the enclosure means (also see FIG. 3). The seal means has communicating therewith discharge passageway 41 and independent conduit means 42. The intake passageway, the discharge passageway, and the independent conduit means, while lying generally in a land 3, or single general plane toward the inner extremity of the enclosure means, ultimately reach three different levels in the seal means as illustrated in FIG. 3. While any arrangement of the three levels may be utilized, as shown in FIGS. 2 and 3, the independent conduit means 42 lie in central plane 43 of the seal means, while the intake passageway 40 lies in lower plane 45 and discharge passageway 41 lies in upper plane 47.

The seal means may be constructed in any desired manner. It is only necessary that the seal means allows the suspended red blood cells to enter the enclosure means, the separate liquid to be discharged from the enclosure means and the separated red blood cells be unloaded from the enclosure means, in a manner that isolates these flows from leakage or contamination. Beyond this, the seal means (and in combination with the injector means) may be as desired. However, the general mode of construction of a seal means as described in the above-identified co-pending application is quite suitable. In the present device, it will be necessary to provide for three separate planes as opposed to the two separate planes of the co-pending application. Nevertheless, conveniently the seal means may be manufactured by providing five annular discs, 50, 51, 52, 53, and 54. These discs are suitably made of a thermo-plastic, such as nylon, polypropylene, polyethylene, polystyrene and the like. Discs 51, 52, and 53 have ports 55 for passing fluids therethrough. The ducts and conduits of the enclosure may be formed by, e.g., heat sealing, ultra-sonic sealing, glue sealing, etc. three films or sheets of plastic, of the nature noted above, with a system of parallel and spaced seals, as disclosed in the co-pending application, which will, of course, provide ducts and conduits. The interior annular portion of those films or sheets may be placed between the respective disc 50-54 and the entire assembly of films (or sheets) and discs is then sealed together. For conciseness, and clarity, only the ducts and conduits are shown in FIG. 3 and remaining portions of the films are omitted from the drawing. Also, not all of the ducts and conduits are shown in FIG. 3 in order to preserve clarity. Additional details are disclosed in the co-pending application, identified above.

By the correct choice of plastic films or sheets, the red blood cell receiving means may also be formed by sealing the outermost periphery and the inner periphery (82 and 83 of FIG. 5) of the plastic films or sheets and then heat-vacuum forming or rotational casting that sealed area to form the red blood cell receiving means. This forming step will also allow the preserving of the passageways described above. Of course the sheet or film in the middle may terminate at the inner periphery.

These techniques are well known to the art and need not be described in detail herein.

As best illustrated in FIG. 3, the injector means 9 fits within the annular space 56 of the seal means 8. It will be noted that when injector 9 is placed within the seal means 8, opposite the juncture of the disc 50/51, 51/52, 52/53 and 53/54 where the plastic film is sealed, there are areas for liquid-tight sealing between the discs in order to prevent intermingling of the liquids at the three different levels. These areas of sealing 57 may be only on the inside of the seal means and have thereon a separate sealing material, such as rubber "O" rings, metal slip rings or the like, in order to promote the sealing between the different levels. Correspondingly, injector 9 may have sealing rings 60 which mate with the sealing areas 57 to effect sealing between the sealing means and the injector. Suitably, these O rings 60 may be of a deformable material of low friction, such as a polypropylene, polyethylene, nylon, polytetrafluoroethylene and the like. A deformable nature will provide effective sealing and yet reduce sliding friction between the injector means and the sealing means. In this arrangement, the injector will remain stationary and the sealing means, in combination with the enclosure means, will rotate thereabout by action of rotatable tables 20 and 21 holding the enclosure means.

Injector 9 has internally therein conduits 61 which connect with the respective passageways 10, 11 and 12 open into ports 62, which ports, of course, correspond with ports 55 of sealing means 8 for passage of the respective fluids in and out of the enclosure means.

Injector 9 may be made of any suitable material, such as metal or plastic. It is only necessary that it be capable of sterilization. For example, a solid plug of nylon may be drilled and tapped for providing the ports and passages and turned to provide grooves for holding "O" rings 60. The injector may then be held into the enclosure means by any suitably or convenient mechanical device. For example, a retaining ring may be placed at both the top and the bottom of the injector means, if desired. The injector means is held in a stationary manner during rotation of the enclosure means and sealing means by any desired mechanical restraint (not shown). Suitably, a bracket, bolt, screw or plate will co-act with the injector means and one of the tables 20 or 21 to hold the injector means in a stationary manner.

It should be understood that the particular shape of blood cell receiving means 2 may vary considerably. FIG. 4 illustrates various shapes which may be used, and, indeed, combinations of the shown or other shapes may be used. In that figure, the first view of the illustrated shapes shows the front view and the "prime" view shows the side view.

The shapes illustrated in FIG. 4 are not limiting of the configurations which may be used with the present invention but simply indicate the breadth of different configurations which are indeed acceptable. It should be noted, specifically, that the outer extremity 70 of blood cell receiving means 2 (also see FIG. 2) may be angularly shaped, or in the form of a semi-circle or eliptically shaped or in a somewhat square or rectangular shape. However, it can be appreciated that it is important to remove as many of the separated and compacted red blood cells as possible from the enclosure means after the separation has been completed. Since the red blood cells may exit from the enclosure means via independent conduit 42, it is preferred that opening 71 terminates rather closely to the outer extremity 70 of the enclosure means. Otherwise, the volume of compacted red blood cells which will remain between the outer extremity 70 and the opening 71 could reach a significant amount of the total volume of compacted red blood cells. For this reason, it is preferred that the volume defined by the outer extremities of the walls of the red blood cell receiving means and a vertical plane 72 of the opening of the independent conduit means be small compared with the total volume of the receiving means, i.e., no more than 20% of the total volume of the receiving means, and especially less than 15% or 10%. Usually this percentage will be from 0.1% to 5%, e.g., 0.5% to 3%. For this reason, it is preferred that there be at least some outwardly extending curvature in the outer extremity of the receiving means, including a curvature of the red blood cell receiving means which has an angularly shaped outer extremity. In this latter regard, it will be noted that the receiving means shown in FIG. 2 has an outer extremity which is an arc of the diameter corresponding to the diameter of the enclosure means on which that outer extremity lies.

However, opening 71 of independent conduit means 42 may lie anywhere in the red blood cell receiving means, including at the inner peripheral extremity (see 83 of FIG. 5), when provisions are made to move the separated red blood cells to that opening for unloading, e.g., a collapsible red blood cell receiving means, as discussed more fully hereinafter.

Also note that duct 4 (which is composed of entry ducts 6 and exit duct 5) is disposed at the innermost extremity of the blood cell receiving means. In order to minimize the volume in the blood cell receiving means which will contain the suspending liquid and other formed elements, the percentage of volume of duct 4 and the receiving means not occupied by red blood cells (see red blood cell level 88 in FIG. 5) based on the total volume of the enclosure means must be small. This percentage should be less than 40% of the volume of the red blood cell receiving means, especially 20% or 15% or less, and usually from 0.1% to 10%, e.g., from 0.5% to 8%. These percentages can be insured by small ratios of entry/exit duct cross-sectional area to the cross-sectional area of the receiving means, i.e., from at least 1:2 and even at least 1:10, e.g., up to 1:200.

The foregoing is better illustrated in FIG. 5, which figure is an enlargement of a portion of the FIG. 2 along line B—B. This figure also serves to illustrate the principle by which the present invention functions. Intake passageway 40 introduces the red blood cells 79 from the seal means and injector to the first red blood cell receiving means 80. As the flow of suspended red blood cells encounters that receiving means at its entry duct 6, the cross-sectional area for flow is greatly increased and the velocity of the red blood cells and suspending liquid greatly decreases. Since the enclosure means is being rapidly rotated to accomplish the centrifugal force, the more dense red blood cells gravitate (or elutriate) in the direction of the centrifugal force, i.e., toward the outer extremity 82 of receiving means 80. The less dense suspending fluid and other formed elements tend to gravitate (elutriate) toward the inner extremity 83 of receiving means 80 and by virtue of being displaced by the growing volume of red blood cells being separated and compacted toward the extremity 82 of receiving means 80. (See McEwen et al *Separation of Biological Particles by Centrifugal Elutriation*, Analytical Biochemistry. Vol. 23, No. 3, June 1968, for a detailed explanation of the mechanism of elutriation.) As the volume of red blood cells in receiving means 80 increases, at some point spillover from that receiving means will occur at first exit duct 84 and that spillover will pass through first entry duct 85 of the second enclosure means 86 where the same process will be repeated, as diagrammatically illustrated in FIG. 5. Similarly, in succession, each receiving means will receive suspended red blood cells, will begin to fill and at some point will cause spillover into the next succeeding enclosure means.

However, since the more dense red blood cells move toward the extremities 82, the less dense suspending fluid will continually be displaced toward the inner extremities 83 and in turn will move through the ducts between succeeding enclosure means in the direction shown by arrow 87.

During operation of the device, the red blood cells which are separated and compacted into receiving means 80 will eventually fill that receiving means as indicated by red blood cell level 88. At this point entering suspended blood cells by-pass receiving means 80 and are separated in succeeding receiving means 86, until that receiving means is also filled. Thereafter, of course, filling will take place in succeeding receiving means.

It should be understood, however, that some separation and compaction will take place in succeeding receiving means before the last preceeding receiving means is filled or even for that matter before the next to last receiving means is filled. It should also be appreciated that as the receiving means 80 fills and as the suspending liquid passes from that receiving means into exit duct 84, the velocity of the suspending liquid will greatly increase due to the decrease in cross-sectional area of that duct, as compared with the available cross-sectional area in receiving means 80. This increase in velocity of suspending liquid tends to sweep away lighter components which are gradually displaced toward the inner extremity 83 as the more dense red blood cell fill the available space in receiving means 80. In this manner, the suspending liquid and lighter elements of the blood, e.g., leukocytes, other formed elements, etc., are moved through the device from one receiving means to the next succeeding receiving means and this mechanism is defined herein as "trans-elutriation". Further, as that next succeeding means begins to fill, as explained above, the suspending liquid and lighter formed elements are again "trans-elutriated" to the next succeeding receiving means.

Finally, the suspending liquid and some of the lighter components will commence exiting the device via discharge passageway 41 which connects with the last receiving means 90. It should be appreciated that for illustration purposes, the total enclosure means is shown as a single unit in a circular configuration. However, in practice, it is preferred that two identical units be used, as shown in FIG. 2, since this supplies balance requirements. Of course, a single unit, as illustrated in FIG. 5, could be used if mechanical counter balancing is provided or if two complete units are stacked in tandem and arranged such that filling of the tandem units are from opposite sides of the tandem arrangement, much in the way illustrated in FIG. 1 for the dual one level unit.

From the foregoing, it will also be appreciated that the present "trans-elutriation" takes place, in part, by the more dense red blood cells essentially filling successive receiving means and causing displacement of the lighter suspending fluids and lighter formed elements so that they may be trans-elutriated through the unit. It will also therefore, be appreciated that the volume of red blood cells fed to the device must be essentially the same as the volume available in the receiving means. If the volume of red blood cells is greater than the available volume in the receiving means, then the last receiving means 90 will fill with red cells and spill red cells out thereof via discharge passageway 41. This, of course, would be wasteful of the red cells, and contaminates the separated leukocytes and platelets, which may themselves be recovered for other known uses.

On the other hand, if the red cells do not essentially fill all of the receiving units, then the latter receiving means will contain suspending liquid and the lighter other formed elements which have not been displaced toward the inner extremities of that receiving means and therefore not available for trans-elutriation out of the device. When the device is subsequently emptied the receiving means which were not filled with red cells will empty into the provided collecting receptical some of the suspending liquid and the unwanted lighter formed elements.

To avoid either of these two unwanted occurrences, it is necessary to determine the volume of red cells to be processed and to insure that the total available volume of the receiving means in any particular device closely matches that volume. It is also well known in the art that the red cell volume per unit of blood (500 mls) varies from individual to individual and between the sexes. This red cell volume is referred to as a hematocrit. A hematocrit may be defined as the packed red cell volume in relationship to 100% of the volume of blood being tested. For example, the hematocrit for women ranges between 38% and 42%. This means that for every 100 mls of whole blood the separated red blood cells will occupy 38 to 42 mls. The hematocrit for men varies from about 41% to 52%.

As is also the standard practice in the art, units of blood received from one donor are never mixed with units of blood from other donors. The purpose of this is to avoid one unit of blood which may be contaminated with virus and the like from equally contaminating many other units of blood which might otherwise be free of unwanted contaminants. Therefore, it is conventional in the art to always process an individual blood donation as a single unit. For this reason, the volumetric capacity of all of blood cell receiving means will essentially equal the packed red cell volume of one unit of blood so that one unit of blood may be effectively processed in one enclosure. After processing that unit of blood, the enclosure, which is disposable, will be simply discarded.

In practice, the hematocrit of a particular unit of blood is determined and essentially matched in volume to one of a series of enclosure means having different total volume of the receiving means. For example, a total receiving means volume of 190 mls will correspond to a hematocrit of 38. This volume may be used for hematocrit of 38 or 42 without excessive red cell loss. Likewise, a receiving means volume of 215 mls will correspond to a hematocrit of 43, but may be used for hematocrit of from 43 to 47. Similarly, a receiving means volume of 240 mls will correspond to a hematocrit of 48, but may be used for hematocrits of from 48 to 52. With these three sizes corresponding to hematocrits of 38, 43, and 48, a range of hematocrits from 38 to 52 may be accommodated. It will be understood that the receiving means volume will always be equal to or less than the volume or packed red cells in order to avoid any available space in the receiving means where unwanted suspending liquid or formed elements may reside.

Alternatively, the last three receiving means may be of a predetermined volume, each with a volume increment corresponding to the three above-identified volume increments and each with a by-pass to the discharge passway which by-pass is openable and closeable, e.g. an externally pressed clamp. A similar clamp is disposed on the exit duct of each of these last three enclosure means. By, thus, operating the clamps, the correct volumes for the three above-noted hematocrits may be achieved with a single enclosure means.

Alternatively, when only one size of enclosure means is desired, this may be accomplished by either closing, e.g. clamping, or eliminating the independent conduit means in as many of the latter red blood cell receiving means as necessary to provide the correct receiving means volume, usually only the last receiving means. Thus, any material collected in these last receiving means will not be recovered and will be discarded with the disposing of the enclosure means. However, by sizing the volume of the remaining receiving means to correspond to a minimum hematocrit, for example 38, all but the last receiving means will be filled with red blood cells and proper trans-elutriation, as explained above, will take place. The last receiving means will collect excess red blood cells and lighter formed elements, e.g., leukocytes and platelets, which will simply remain in the disposed enclosure means. Of course, this embodiment is used only when it is not desired to recover the lighter formed elements. Where these elements are to be recovered, the volume of the receiving means used should accurately equate with the packed red cell volume fed to the centrifuge. Further, the last one or two receiving means may be of substantially smaller size and, consequently, the smaller upper layer surface area (see 88 of FIG. 5) maximizes the fractionation of red cells from the lighter formed elements.

The separated and compacted red blood cells may be freed from suspending liquid (which contain leukocytes and the like) by flushing duct 4 (composed of exit duct 5 and entry duct 6 as shown in FIG. 2) with a wash fluid which will sweep away the suspending liquid above the red blood cells. This is accomplished by passing a wash fluid through the injector means and intake passageway 40 after the receiving means had been filled with red blood cells. This will cause a sweeping of the space between the red blood cell level and the inner extremity of the receiving means (see 88 and 83, respectively, in FIG. 5). This sweeping will wash away the suspending liquid and replace that suspending liquid with the wash fluid. The wash fluid may be, suitably, as salinic solution or an autologous cleansed plasma. It will be appreciated, however, that since this wash only sweeps that limited space, it is not necessary for a large volume of wash fluid to be passed therethrough. A volume of wash fluid at least equal to the volume between the compacted cells and the inner extremities will generally be sufficient, but more often twice or three times that volume is preferred. The salinic solutions are well known in the art and need not be described herein. In lieu of salinic solution or plasma, glucose-saline solutions, heat inactivated human serum albumin or other transfusionable solutions may be used.

It should also be fully understood that while it is not normally desired to operate the present device so that the separated and compacted blood cells are again resuspended, the device may be so operated. In this embodiment, the red blood cells are re-suspended for flowing out of the device by first washing the space between the compacted blood cells and the inner-most extremities, as noted above. A fluid is then injected into the enclosure means via the pathway of the liquid suspended red blood cell and this facilitates removal of the separated red blood cells from the receiving means via the independent conduit means. On the other hand, this pathway may be reversed and the fluid may be injected via the independent conduit means and the re-suspended red blood cells may be removed from the enclosure means via the intake passageway. In either case, the centrifuge is stopped or slowed in order to remove the red cells.

As shown in FIG. 2, the enclosure means may actually comprise a number of identical enclosure means which in combination form a circular configuration. In the case of FIG. 2, there are two identical enclosure means. However, any number of identical enclosure means may be used, but at least two and preferably at least four receiving means will be used, e.g., 2 to 100 but more often 2 to 24 and more usually 4 to 12, especially 6 to 10. Usually, in combination they form a circular configuration, although this is not absolutely necessary. Of course, means must be provided whereby each enclosure means is simultaneously operated (loaded and unloaded) so that the total enclosure means remain in dynamic balance. In this case, the injector means must be so controlled that the total volume of suspended red blood cells to be passed to the enclosure means is equally split between each of the enclosure means (also shown in FIG. 2). Of course, the total number of enclosure means must have a total volume of all red blood cell receiving means which is consistent with the packed red blood cell volume (hematocrit) of the red blood cells in the total liquid fed to the number of enclosure means, as explained above.

The enclosure means is conveniently unloaded of separated and compacted red blood cells by applying a differential pressure across collapsible enclosure means. Most conveniently, a vacuum is drawn on the inside of the enclosure means via the independent conduit means. This forces red blood cells from the enclosure means through the seal means and out of the injector means. At the same time, the collapsible enclosure means contracts toward the opening 71 (see FIG. 4) of independent conduit means 42 and further forces the last remaining red blood cells into independent conduit means 42 and out of the device. Alternately, a bleed of sterile air may be introduced into the enclosure means via either intake or discharge passageways 40 and 41. This will allow for a controlled movement of the red blood cells out of the enclosure means by varying the amount of replacement air. The rate in which the red blood cells are removed from the enclosure means may be correspondingly controlled.

Of course, when the last receiving means is used as a collector for excess red blood cells and unwanted solid blood components, the contents of that last receiving means should be prevented from contaminating the recovered red blood cells. This can be accomplished provided by a check valve between the entry duct of the last receiving means and the exit duct of the next to last receiving means. Also, that last receiving means will not have an independent conduit means. Alternatively, or in addition, elutriated excess red blood cells and unwanted solid blood components may be collected outside of the enclosure means by providing a recepticle therefore which is in fluid communication with passageway 41 and unloading duct 10.

The centrifuge may be rotated by any desired mechanical means and conventional electric motors are quite suitable in this regard. This introduction of the suspended red blood cells, the removal of the suspending liquid and the trans-elutriated leukocytes and other unwanted lighter formed blood elements and components are accomplished with conventional pumps and valve control means well known in the art. Suitable control means of this nature are described in the above-identified co-pending application. Also see U.S. Pat. Nos. 3,737,096 to Jones et al, issued June 5, 1973; 3,858,796 to Unger, issued Jan. 7, 1975; 3,864,089 to Tiffany, et al, issued on Feb. 4, 1975, for illustrations of suitable control means. Details of mechanical centrifuge devices suitable for the present invention may be found in U.S. Nos. 3,672,546 to Schultz, issued June 27, 1972; 3,561,672 issued to Schultz on Feb. 9, 1971; 3,674,197 issued to Mitchell on July 4, 1974; 3,452,924 issued to Schultz on July 1, 1969.

The control means is composed of conventional elements arranged in conventional manners, all of which are well known in the art. These control means include timers, electrically operated solenoids, governors for speed control, flow meters, and the like. The control means controls the flow of liquid suspended blood cells through the injector means by virtue of timed solenoid operated automatic valves or clamps. Of course, the suspended blood cells then inherently flow through the intake passageway and entry duct into the first blood cell receiving means and the succeeding trans-elutriation takes place automatically. The control means also controls the flow of suspending liquid and unwanted formed elements from the exit duct means of the last blood cell receiving means through the discharge passageway and through the injector by way of a conventional pump operated with throttling solenoid valves. If desired, the entire apparatus may be first filled with salinic solution or the like to afford priming of such pump. If this is accomplished, then the requirement for dynamic balance is filling the suspended blood cells into the enclosure means is substantially reduced. Similarly, the control means operates for controlling the flow of separated red blood cells from the blood cell receiving means through the independent conduit means through the injector by way of a vacuum pump which removes the red blood cells from the device as controlled by throttling solenoid operated valves. Here again, a throttling solenoid operated valve or clamp may control the replacement by sterile air for the purposes discussed above. All of these functions can be on a timed basis (operated by a timer), when the operation is in connection with a specific volume of blood and the timers have been preset to accomplish the correct cycles of the device for that set volume of blood. Automatic timers of this nature are well known in the art and need not be discussed in any detail.

Thus, the control means functions so that the liquid suspended red blood cells move from the injector means to the first red blood cell receiving means and by centrifugal force the more dense red blood cells separate from the less dense suspending liquid and compact at the periphery of the extremity of the red blood cell receiving means. Red cells and suspending liquid (with leukocytes, platelets and other unwanted lighter formed blood elements and components) is trans-elutriated via the exit duct means of the first red blood cell receiving means and the entry duct means in the next succeeding red blood cell receiving means into the next succeeding red blood cell receiving means. That function is repeated in each succeeding red blood cell receiving means so that essentially total separation of the red blood cells from the suspending liquid, leukocytes, platelets and cellular debris is accomplished.

As noted above, the materials of construction for the enclosure means can be chosen as desired, so long as the materials will withstand sterilization. Suitably, the enclosure means is constructed of a polymeric material, e.g., a plastic resin, such as a polyolefin (polyethylene, polypropylene, polypentene), polyvinyl chloride, polyvinylidene chloride, polyvinyl acetate, polystyrene, polyacrylate (such as polymethyl methacrylate), polyester, polyamide (such as nylon 6 or nylon 66), polysiloxane, polycarbonate, polyacetate or butyrate, natural or synthetic rubbers and combinations thereof. Similarly, the seal means and injector may be made of such polymeric materials. Preferably, the films and seal means are made of a thermoplastic polymeric material, although this is not required.

The enclosure means is held within the cavity of the centrifuge (illustrated in FIG. 1) and is rotated at the first lower angular speed about its vertical axis while loading is commenced. After loading has begun to take place, the angular speed of the centrifuge is increased to operational speeds. Alternatively, operational speeds may be commenced during the initial loading procedure. The speed of angular rotation is maintained such that sufficient centrifugal force is exerted on the suspended red blood cells to separate and compact the cells in the receiving means and trans-elutriation is accomplished. Thereafter, the angular speed of rotation of the enclosure is reduced so that the compacted and separated red blood cells in the receiving means may be removed therefrom, as explained above. The particular angular speeds of rotation can vary considerably depending upon the specific diameter of the enclosure means. Obviously, for a larger diameter enclosure means, sufficient centrifugal force will be developed at a much lower angular speed than will be required for smaller diameter enclosure means. However, as an indication of appropriate speeds, sufficient centrifugal force will be developed in a 12-inch diameter enclosure means when the angular speed is between about 1500 and 5000 revolutions per minute, more often between 2000 and 4000 revolutions per minute, e.g., around 3000 revolutions per minute. The speed of angular rotation during the unloading may be much lower than during the separation step. Low angular rotations of 50 to 200 revolutions per minute will aid in removing the red blood cells via the independent conduit means by virtue of causing movement of the last cells toward the opening at the outer extremity of the independent conduit means.

The temperature at which the device is operated is not critical and may suitably be at any temperature above the freezing point or coagulation point of the suspended red blood cells and below the denaturing point of the red blood cells, in any case. Generally, temperatures between 40° F and 100° F are satisfactory, especially between 60° F and 90° F. For prolonged repetitive use, refrigeration of the centrifuge may be required to remove mechanically produced heat and maintain these temperatures. Suitably, the tables 20 and 21 may be so cooled or the device may be operated in a cooled room.

As noted above, tandem arrangements of the enclosure means may be used as desired. Thus, a stack of two or more enclosure means may be contained in a single or cooperating group of rotation means. Where a group of rotation means is used, this requires physical interlocking of the cooperating rotation means so that they may be operated by a single power means and under control of a single control means. Otherwise, the operation of the enclosure means in this tandem arrangement will be as described above. Alternately, a plurality of the enclosure means may be disposed within a single rotation means. This would only require that the seal means and injector means have mirror image arrangements for receiving an enclosure means in the lowermost part and an enclosure means in the upper most part of the mirror image arrangements. This will allow, quite easily, a tandem of two enclosure means. Yet further, a plurality of enclosure means may be stacked upon each other where the enclosure means are generally in the arrangement of FIG. 1 and a common injector means passes through the seal means of each of the enclosure means (with the exception of, of course, the last under enclosure means). By use of spacers to position the enclosure means along this common injector means, the single control means may be used for performing all the functions of a plurality of enclosure means.

The foregoing describes the invention in terms of separating red blood cells and this is an important embodiment. The separated red blood cells are essentially free of leukocytes and platelets. The term "essentially free" means that the amount of leukocytes and platelets contaminating the separated red cells will not usually produce a substantial hological response when injected into humans, e.g. no measurable increase in clotting will occur in the case of contaminating platelets. The red cells may, therefore, be supplied in a packed form or in a liquid suspended form, e.g., in a salinic solution, as discussed above.

However, it should be appreciated that the invention is not limited to the separation of red blood cells, but extends to the separation of more dense solids from a mixture of a suspending fluid and/or less dense solids. A solid is defined herein as any physically separatable matter and includes, settleable solids, suspended solids, colloidal solids, cells and formed elements of blood, e.g., platelets, granulocytes (polymorpho-nuclear), lymphocytes, monocytes, etc.

An example of the foregoing is the separation of the "buffy coat" components from blood plasma. The red cells may be separated, as discussed above, and the recovered plasma will have substantial quantities of the "buffy coat" therein. After the volume of the solids in the plasma is determined, the correct volume of receiving means is provided and the "buffy coat" solids are separated from the plasma in the same manner described above. The "buffy coat" solids contain solids of different densities and it will be appreciated that the more dense solid will principally collect in the first several receiving means and the less dense solids will collect in the latter several receiving means. This, in effect, also selectively separates solid components.

Thus, as a broader embodiment of the invention both the method and apparatus are equally applicable to suspensions, as noted above. The present specification, therefore should be construed in the manner that the disclosure toward separating of red blood cells is the same for separating the suspensions of a more dense solid from a suspending liquid and, often, from a less dense solid.

The method of the invention includes the separating of red blood cells (or a suspension as discussed above) from a suspending liquid wherein the step includes flowing liquid suspended red blood (or more dense solids suspension) into a first red blood cell receiving means (or suspension receiving means) of an enclosure means which has a plurality of red blood cell receiving means in fluid communication with each other and spaced about the vertical periphery of the enclosure means and forming part of the enclosure means. Each of the red blood cell receiving means has an entry duct means for passing liquid suspended blood cells into the receiving means and an exit duct means for passing from the receiving means suspending liquid which has been at least partially depleted of red blood cells. The exit duct means of each blood cell receiving means is in fluid communication with the entry duct means of the next succeeding red blood cell receiving means. The entry and exit duct means are of a vertical cross-sectional area which is small compared with the vertical cross-sectional area of the receiving means and the peripheral extremity of the receiving means lies on a peripheral diameter of the enclosure means which is larger than the peripheral diameters of the enclosure means on which the peripheral extremities of the entry and exit duct means lie. The enclosure means is rotated about the vertical axis thereof at a speed of angular rotation such that sufficient centrifugal force is exerted on the red blood cells (or more dense solids) to separate the red blood cells from the suspending liquid and compact the red blood cells at the peripheral extremity of the first red blood cell receiving means. The suspending liquid is trans-elutriated via the exit duct means of the first red blood cell receiving means and the entry duct means of the next succeeding red blood cell receiving means into the next succeeding red blood cell receiving means. This function is repeated with each succeeding red blood cell receiving means and essentially total separation of the red blood cells from the suspending liquid is accomplished. Suspending liquid is removed from the enclosure means and additional liquid suspended red blood cells are flowed into the enclosure means until all emptiable red blood cell receiving means are substantially filled with red blood cells. Thereafter, the red blood cells are removed and recovered from the emptiable red blood cell receiving means.

As can be appreciated from the foregoing, the most basic feature of the invention is the trans-elutriation function. In the usual centrifuge, particles are simply elutriated, i.e. are moved from a position closer to the axis of rotation to a position more distanal from the axis of rotation essentially along a radial pathway. In trans-elutriation, as explained above, suspending liquids, contaminants, and unwanted lighter solids are also elutriated essentially along a circumferential pathway, i.e. a trans-pathway, which is identified herein as trans-elutriation. Since during filling of the enclosures, some of the suspended particles are also trans-elutriated and collected in a succeeding enclosure, this results in a highly effective separation of the particles with little contaminating liquids or solids.

Other modifications will be further apparent and the claims are intended to embrace those modifications.

What is claimed is:

1. A centrifuge apparatus for separating red bood cells from a suspending liquid comprising:

(1) enclosure means for enclosing liquid suspended red blood cells;

(2) rotation means for rotating the enclosure means about the vertical axis thereof;

(3) injector means for moving the liquid suspended blood cells into and the separated blood cells out of the enclosure means;

(4) seal means for sealing the injector means to the enclosure means in a liquid-tight relationship;

(5) plurality of red blood cell receiving means in fluid communication with each other and spaced about the longitudinal periphery of the enclosure means and forming part of the enclosure means; wherein each of the red blood cell receiving means has an entry duct means for passing liquid suspended blood cells into the red blood cell receiving means and an exit duct means for passing from the red blood cell receiving means suspending liquid which has been at least partially depleted of red blood cells, the exit duct means of each red blood cell receiving means being in fluid communication with the entry duct means of the next succeeding red blood cell receiving means; and wherein the entry and exit duct means are of a vertical cross-sectional area which is small compared with the vertical cross-sectional area of the red blood cell receiving means and the peripheral extremity of the red blood cell receiving means lies on a peripheral diameter of the enclosure means which is larger than the peripheral diameters of the enclosure means on which the peripheral extremities of the entry and exit duct means lie;

(6) an intake passage means in fluid communication with the injector means for passing liquid suspended red blood cells from the injector means into the entry duct of a first red blood cell receiving means;

(7) a discharge passage means in fluid communication with the injector means for passing suspending liquid from the exit duct means of the last red blood cell receiving means to the injector means;

(8) a plurality of independent conduit means, reach with one end thereof in fluid communication with the said injector means and the other end thereof disposed in the red blood cell receiving means;

(9) power means for rotating the rotation means and enclosure means to a speed of angular rotation sufficient to separate the red blood cells from the suspending liquid and compact the red blood cells in the red blood cell receiving means;

(10) control means for controlling the flow of liquid suspended blood cells through the injector means, intake passage means and entry duct of the first red blood cell receiving means; for controlling the flow of suspending liquid from the exit duct means of the last red blood cell receiving means through the discharge passage means and through the injector; and for controlling the flow of separated red blood cells from the red blood cell receiving means through the injector and out of the apparatus injector;

whereby the apparatus functions so that liquid suspended red blood cells move from the injector means to the first red blood cell receiving means and by centrifugal force the more dense red blood cells separate from the less dense suspending liquid and compact at the peripheral extremity of the red blood cell receiving means and the suspending liquid trans-elutriated via the exit duct means of the first red blood cell receiving means and the entry duct means of the next succeeding red blood cell receiving means into the next succeeding red blood cell receiving means, and whereby said function is repeated with each succeeding red blood cell receiving means and essentially total separation of the red blood cells from the suspending liquid is accomplished.

2. The apparatus of claim 1 wherein the control means includes wash means for washing the separated blood cells by passing a washing fluid through the apparatus in the same flow path as the path of the suspended red blood cells.

3. The apparatus of claim 1 wherein the enclosure means is collapsible.

4. The apparatus of claim 3 wherein the control means included a pressure differential means for inducing a pressure differential between the outside and inside the enclsoure means whereby the enclosure means collapses and forces the separated blood cells out of the enclosure means via an independent conduit means.

5. The apparatus of claim 1 wherein the enclosure means is disposable.

6. The apparatus of claim 1 wherein the entry duct means and the exit duct means are a single opening between adjoining red blood cell receiving means.

7. The apparatus of claim 4 wherein the end of the independent conduit means which is disposed in the red blood cell receiving means is at least near the peripheral extremity of the red blood cell receiving means.

8. The apparatus of claim 1 wherein the suspending liquid also contains other formed blood elements and these formed elements are separated from the red blood cells and are trans-elutriated with the suspending liquid.

9. The apparatus of claim 1 wherein the ratio of vertical cross-sectional area of the entry and exit duct means to the cross-sectional area of the receiving means is at least 1:2.

10. The apparatus of claim 9 wherein the said ratio is at least 1:3.

11. The apparatus of claim 9 wherein the said ratio is at least 1:6.

12. The apparatus of claim 1 wherein the peripheral extremity of the receiving means lies on a peripheral diameter of the enclosure means which is at least 5% larger than the peripheral diameters of the enclosure means on which the entry and exit ducts lie.

13. The apparatus of claim 1 wherein the peripheral extremity of the receiving means lies on a peripheral diameter of the enclosure means which is at least 10% larger than the peripheral diameters of the enclosure means on which the entry and exit ducts lie.

14. The apparatus of claim 1 wherein the volume of each receiving means is at least twice as large as the volume of the duct means.

15. The apparatus of claim 1 wherein the volume of each receiving means is at least four times as large as the volume of the duct means.

16. The apparatus of claim 1 wherein the volume defined by the outer extremities of the wall of the red blood cell receiving means and a vertical plane at the opening of the independent conduit means in the red blood cell receiving means is no more than 20% of the total volume of the red blood cell receiving means.

17. The apparatus of claim 1 wherein the volume defined by the outer extremities of the wall of the red blood cell receiving means and a vertical plane at the opening of the independent conduit means in the red blood cell receiving means is no more than 15% of the total volume of the red blood cell receiving means.

18. The apparatus of claim 1 wherein the outer extremity of the red blood cell receiving means has an outwardly extending curvature.

19. The apparatus of claim 18 wherein the curvature is outwardly and angularly shaped.

20. The apparatus of claim 1 wherein the volume of the entry duct, the exit duct and the volume of the red blood cell receiving means which is not occupied by red blood cells is less than 30% of the volume of the red blood cell receiving means.

21. The apparatus of claim 1 wherein the volume of the entry duct, the exit duct and the volume of the red blood cell receiving means which is not occupied by red blood cells is less than 20% of the volume of the red blood cell receiving means.

22. The apparatus of claim 1 wherein there are 2 to 24 red blood cell receiving means.

23. The apparatus of claim 1 wherein there are 4 to 12 red blood cell receiving means.

24. The apparatus of claim 4 wherein the control means includes a fluid injection means for injecting a fluid into the enclosure means via the pathway of the liquid suspended red blood cells to facilitate the removal of the separated red blood cells from the red blood cell receiving means.

25. The apparatus of claim 1 wherein ther are an even number of identical enclosure means which in combination form a circular configuration and control means are provided whereby each enclosure means is simultaneously operated so that the total circular configuration remains in dynamic balance.

26. The apparatus of claim 25 wherein the injector means is controlled by the control means such that the total volume of suspended red blood cells to be passed to the number of enclosure means is equally split between each of the said enclosure means.

27. The apparatus of claim 1 wherein the total volume of all blood cell receiving means is substantially equal to the packed red blood cell volume of the red blood cells in the total liquid fed to the enclosure means.

28. The apparatus of claim 1 wherein the total volume of all blood cells receiving means, except the last said receiving means, is substantially equal to the packed red blood cell volume of the red blood cells in the total liquid fed to the enclosure means and said last blood cell receiving means does not have an independent conduit means but serves as a disposable collector for unwanted solid matter separated from the red blood cells.

29. The apparatus of claim 1 wherein the centrifugal force is also sufficient to separate other formed blood elements from the red blood cells.

30. The apparatus of claim 29 wherein the other formed elements are trans-elutriated out of the apparatus with the suspending liquid.

31. A method for separating red blood cells from a suspending liquid comprising:
(1) flowing liquid suspended red blood cells into a first red blood cell receiving means of an enclosure means which has a plurality of red blood cell receiving means in fluid communication with each other and spaced about the longitudinal periphery of the enclosure means and forming part of the enclosure means and wherein each of the red blood cell receiving means has an entry duct means for passing liquid suspended blood cells into the red blood cell receiving means and an exit duct means for passing from the red blood cell receiving means suspending liquid which has been at least partially depleted of red blood cells, the exit duct means of each red blood cell receiving means being in fluid communication with the entry duct means of the next succeeding red blood cell receiving means and wherein the entry and exit duct means are of a vertical cross-sectional area which is small compared with the vertical cross-sectional area of the red blood cell receiving means and the peripheral extremity of the red blood cell receiving means lies on a peripheral diameter of the enclosure means which is larger than the peripheral diameters of the enclosure means on which the peripheral extremities of the entry and exit duct means lie;
(2) rotating the enclosure means about the vertical axis thereof at a speed of angular rotation such that sufficient centrifugal force is exerted on the red blood cells to separate the red blood cells from the suspending liquid and compact the red blood cells at the peripheral extremity of the first red blood cell receiving means and the suspending liquid is trans-elutriated via the exit duct means of the first red blood cell receiving means and the entry duct means of the next succeeding red blood cell receiving means into the next succeeding red blood cell receiving means, and whereby said function is repeated with each succeeding red blood cell receiving means and essentially total separation of the red blood cells from the suspending liquid is accomplished;
(3) removing suspending liquid from the enclosure means and flowing additional liquid suspended red blood cells into the enclosure means until all emptiable red blood cell receiving means are substantially filled with red blood cells; and
(4) removing and recovering the red blood cells from the emptiable red blood cell receiving means.

32. The method of claim 31 wherein the enclosure means is collapsible and a differential pressure is induced between the outside and inside of the enclosure means whereby the enclosure means collapses and forces the separated red blood cells out of the red blood cell receiving means via an independent conduit means disposed within the red blood cell receiving means.

33. The method of claim 31 wherein the entry duct means and the exit duct means are a single opening between adjoining red blood cell receiving means.

34. The method of claim 32 wherein the end of the independent conduit means which is disposed in the red blood cell receiving means is at least near the peripheral extremity of the red blood cell receiving means.

35. The method of claim 31 wherein the suspending liquid also contains other formed blood elements and these formed elements are separated from the red blood cells and are trans-elutriated with the suspending liquid.

36. The method of claim 31 wherein the ratio of vertical cross-sectional area of the entry and exit duct means to the cross-sectional area of the receiving means is at least 1:2.

37. The method of claim 36 wherein the said ratio is at least 1:3.

38. The method of claim 31 wherein the peripheral extremity of the receiving means lies on a peripheral diameter of the enclosure means which is at least 5% larger than the peripheral diameters of the enclosure means on which the entry and exit ducts lie.

39. The method of claim 31 wherein the volume of each receiving means is at least twice as large as the volume of the duct means.

40. The method of claim 32 wherein the volume defined by the outer extremities of the wall of the red blood cell receiving means and a vertical plane at the opening of the independent conduit means in the red blood cell receiving means is no more than 20% of the total volume of the red blood cell receiving means.

41. The method of claim 31 wherein the outer extremity of the red blood cell receiving means has an outwardly extending curvature.

42. The method of claim 41 wherein the curvature is outwardly angularly shaped.

43. The method of claim 31 wherein the volume of the entry duct, the exit duct and the volume of the red blood cell receiving means which is not occupied by red blood cells is less than 30% of the volume of the red blood cell receiving means.

44. The method of claim 31 wherein there are 2 to 24 red blood cell receiving means.

45. The method of claim 31 wherein a fluid is injected into the enclosure means via the pathway of the liquid suspended red blood cells to remove the separated red blood cells from the red blood cell receiving means.

46. The method of claim 31 wherein there are a plurality of identical enclosure means which in combination form a circular configuration and each enclosure means is simultaneously operated so that the total circular configuration remains in dynamic balance.

47. The method of claim 46 wherein the total volume of suspended red blood cells to be passed to the plurality of enclosure means is equally split between each of the enclosure means.

48. The method of claim 31 wherein the total volume of all blood cell receiving means is substantially equal to the packed red blood cell volume of the red blood cells in the total liquid fed to the enclosure means.

49. The method of claim 31 wherein the total volume of all blood cells receiving means, except the last said receiving means, is substantially equal to the packed red blood cell volume of the red blood cells in the total liquid fed to the enclosure means and said blood cell receiving means serves as a disposable collector for unwanted solid matter separated from the red blood cells.

50. The method of claim 31 wherein the speed of angular rotation is at least 1500 revolutions per minute.

51. A method for separating a more dense solid from a suspension of the more dense solid and the less dense solids in a suspending liquid comprising:

(1) flowing the suspension into a first suspension receiving means of an enclosure means which has a plurality of suspension receiving means in fluid communication with each other and spaced about the longitudinal periphery of the enclosure means and forming part of the enclosure means and wherein each of the suspension receiving means has an entry duct means for passing suspension into the suspension receiving means and an exit duct means for passing from the receiving means suspension which has been at least partially depleted of more dense solids, the exit duct means of each suspension receiving means being in fluid communication with the entry duct means of the next succeeding suspension receiving means and wherein the entry and exit duct means are of a vertical cross-sectional area which is small compared with the vertical cross-sectional area of the suspension receiving means and the peripheral extremity of the suspension receiving means lies on a peripheral diameter of the enclosure means which is larger than the peripheral diameters of the enclosure means on which the peripheral extremities of the entry and exit duct means lie.

(2) rotating the enclosure means about the vertical axis thereof at a speed of angular rotation such that sufficient centrifugal force is exerted on the more dense solids to separate the more dense solids from the suspending liquid and compact the more dense solids at the peripheral extremity of the first suspension receiving means and the suspending liquid is trans-elutriated via the exit duct means of the first suspension receiving means and the entry duct means of the next succeeding suspension receiving means into the next succeeding suspension receiving means, and whereby said function is repeated with each succeeding suspension receiving means and essentially total separation of the more dense solids from the less dense solids and the suspending liquid is accomplished;

(3) removing suspending liquid from the enclosure means and flowing additional suspension into the enclosure means until all emptiable suspension receiving means are substantially filled with more dense solids; and (4) removing and recovering the more dense solids from the emptiable suspension receiving means.

52. The method of claim 51 wherein the enclosure means is collapsible and a differential pressure is induced between the outside and inside of the enclosure means whereby the enclosure means collapses and forces the separated more dense solids out of the suspension receiving means via an independent conduit means disposed within the suspension receiving means.

53. A disposable structure for use in a centrifuge for the separation of red blood cells from a suspending liquid wherein the centrifuge includes means for containing a quantity of liquid suspended red blood cells, a rotation means for rotating the suspended red blood cells about an axis of the rotation means, and control means for flowing the suspended red blood cells into the centrifuge, the separated suspending liquid out of the centrifuge and the separated red blood cells out of the centrifuge comprising:

(1) a disposable enclosure means for enclosing a quantity of liquid suspended red blood cells and adapted and configured to be releasably held by the rotation means in a manner that the enclosure means with liquid suspended red blood cells therein may be rotated by the rotation means, said enclosure means having a plurality of red blood cell receiving means in fluid communication with each other and spaced about the longitudinal periphery of the enclosure means and forming part of the enclosure means; wherein each of the red blood cell receiving means has an entry duct means for passing liquid suspended blood cells into the red blood cell receiving means and an exit duct means for passing from the red blood cell receiving means suspending liquid which has been at least partially depleted of red blood cells, the exit duct means of each red blood cell receiving means being in fluid communication with the entry duct means of the next succeeding red blood cell receiving means; and wherein the entry and exit ducts means are of a vertical cross-sectional area which is small compared with the vertical cross-sectional area of the red blood cell receiving means and the peripheral extremity of the red blood cell receiving means lies on a peripheral diameter of the enclosure means which is larger than the peripheral diameters of the enclosure means on which the peripheral extremities of the entry and exit duct means lie;

(2) an intake passage means in fluid communication with the control means for passing liquid suspended red blood cells from the control means into the entry duct of a first red blood cell receiving means;

(3) a discharge passage means in fluid communication with the control means for passing suspending liquid from the exit duct means of the last red blood cell receiving means to the control means;

(4) a plurality of independent conduit means, each with one end thereof in fluid communication with the said control means and the other end thereof disposed in the red blood cell receiving means;

whereby pathways are established so that liquid suspended red blood cells may move from the control means to the first red blood cell receiving means and by centrifugal force the more dense red blood cells may separate from the less dense suspending liquid and compact at the peripheral extremity of the red blood cell receiving means and the suspending liquid may be trans-elutriated via the exit duct means of the first red blood cell receiving means and the entry duct means of the next succeeding red blood cell receiving means into the next succeeding red blood cell receiving means, and whereby said function may be repeated with each succeeding red blood cell receiving means and essentially total separation of the red blood cells from the suspending liquid may be accomplished.

54. The structure of claim 53 wherein the enclosure means is collapsible.

55. The structure of claim 53 wherein the entry duct means and the exit duct means are a single opening between adjoining red blood cell receiving means.

56. The structure of claim 53 wherein the end of the independent conduit means which is disposed in the red blood cell receiving means is at least near the peripheral extremity of the red blood cell receiving means.

57. The structure of claim 53 wherein the structure is in a liquid tight relationship to an injector means which is cooperable with the control means for passing suspended red blood cells into and separated red blood cells and suspending liquid out of the said enclosure means.

58. The structure of claim 53 wherein the enclosure means and injector means are disposable.

59. The structure of claim 53 wherein the ratio of vertical cross-sectional area of the entry and exit duct means to the cross-sectional area of the receiving means is at least 1:2.

60. The structure of claim 59 wherein the said ratio is at least 1:3.

61. The structure of claim 59 wherein the said ratio is at least 1:6.

62. The structure of claim 53 wherein the peripheral extremity of the receiving means lies on a peripheral diameter of the enclosure means which is at least 5% larger than the peripheral diameters of the enclosure means on which the entry and exit ducts lie.

63. The apparatus of claim 53 wherein the peripheral extremity of the receiving means lies on a peripheral diameter of the enclosure means which is at least 10% larger than the peripheral diameters of the enclosure means on which the entry and exit ducts lie.

64. The structure of claim 53 wherein the volume of each receiving means is at least twice as large as the volume of the duct means.

65. The structure of claim 53 wherein the volume of each receiving means is at least four times as large as the volume of the duct means.

66. The structure of claim 53 wherein the volume defined by the outer extremities of the wall of the red blood cell receiving means and a vertical plane at the opening of the independent conduit means in the red blood cell receiving means is no more than 20% of the total volume of the red blood cell receiving means.

67. The structure of claim 53 wherein the volume defined by the outer extremities of the wall of the red blood cell receiving means and a vertical plane at the opening of the independent conduit means in the red blood cell receiving means is no more than 15% of the total volume of the red blood cell receiving means.

68. The structure of claim 53 wherein the outer extremity of the red blood cell receiving means has an outwardly extending curvature.

69. The apparatus of claim 68 wherein the curvature is outwardly and angularly shaped.

70. The structure of claim 53 wherein the volume of the entry duct, the exit duct and the volume of the red blood cell receiving means which is not occupied by red blood cells is less than 30% of the volume of the red blood cell receiving means.

71. The structure of claim 53 wherein the volume of the entry duct, the exit duct and the volume of the red blood cell receiving means which is not occupied by red blood cells is less than 20% of the volume of the red blood cell receiving means.

72. The structure of claim 53 wherein there are 2 to 24 red blood cell receiving means.

73. The structure of claim 53 wherein there are 4 to 12 red blood cell receiving means.

74. The structure of claim 53 wherein there are an even number of identical enclosure means which in combination form a circular configuration.

75. The structure of claim 53 wherein the total volume of all blood cell receiving means is substantially equal to the packed red blood cell volume of the red blood cells in the total liquid to be fed to the enclosure means.

76. The structure of claim 53 wherein the total volume of all blood cells receiving means, except the last said receiving means, is substantially equal to the packed red blood cell volume of the red blood cells in the total liquid to be fed to the enclosure means and said last blood cell receiving means does not have an independent conduit means but serves as a disposable collector for unwanted solid matter separated from the red blood cells.

* * * * *